United States Patent
Rzany et al.

(10) Patent No.: US 9,095,435 B2
(45) Date of Patent: Aug. 4, 2015

(54) IMPLANTATION DEVICE

(75) Inventors: Alexander Rzany, Nuremberg (DE);
Matthias Fringes, Ansbach (DE);
Alexander Borck, Aurachtal (DE);
Robert Schmiedl, Hirschaid (DE);
Claus Harder, Uttenreuth (DE)

(73) Assignee: BIOTRONIK AG, Buelach (CH)

( * ) Notice: Subject to any disclaimer, the term of this patent is extended or adjusted under 35 U.S.C. 154(b) by 171 days.

(21) Appl. No.: 13/364,639

(22) Filed: Feb. 2, 2012

(65) Prior Publication Data
US 2012/0203331 A1      Aug. 9, 2012

Related U.S. Application Data

(60) Provisional application No. 61/440,425, filed on Feb. 8, 2011.

(51) Int. Cl.
*A61F 2/24*      (2006.01)

(52) U.S. Cl.
CPC .............. *A61F 2/2427* (2013.01); *A61F 2/2418* (2013.01); *A61F 2/243* (2013.01); *A61F 2/2409* (2013.01); *A61F 2230/0065* (2013.01); *A61F 2230/0067* (2013.01); *A61F 2230/0078* (2013.01); *A61F 2250/001* (2013.01); *A61F 2250/006* (2013.01)

(58) Field of Classification Search
CPC ..... A61F 2/2427; A61F 2/243; A61F 2/2439; A61F 2/2436; A61F 2/2409; A61F 2/2418; A61F 2/2445; A61F 2/2442; A61F 2/2448; A61M 3/0291; A61M 25/04; A61B 2017/348

USPC .......... 623/2.11, 2.38, 2.14–2.19, 2.22, 1.22, 623/1.15, 2.36, 2.37; 606/198, 191, 200, 606/213
See application file for complete search history.

(56) References Cited

U.S. PATENT DOCUMENTS

| | | | | |
|---|---|---|---|---|
| 4,042,979 | A * | 8/1977 | Angell | 623/2.37 |
| 5,334,210 | A * | 8/1994 | Gianturco | 606/151 |
| 5,716,397 | A * | 2/1998 | Myers | 623/2.36 |
| 5,861,003 | A * | 1/1999 | Latson et al. | 606/213 |
| 5,976,174 | A * | 11/1999 | Ruiz | 606/213 |
| 6,056,769 | A | 5/2000 | Epstein et al. | |
| 6,312,465 | B1 * | 11/2001 | Griffin et al. | 623/2.38 |
| 6,350,270 | B1 * | 2/2002 | Roue | 606/151 |
| 6,391,037 | B1 * | 5/2002 | Greenhalgh | 606/151 |
| 6,562,058 | B2 * | 5/2003 | Seguin et al. | 606/200 |
| 6,585,748 | B1 * | 7/2003 | Jeffree | 606/200 |
| 6,730,121 | B2 * | 5/2004 | Ortiz et al. | 623/2.17 |
| 6,846,316 | B2 * | 1/2005 | Abrams | 606/200 |
| 6,932,830 | B2 * | 8/2005 | Ungs | 606/200 |
| 7,033,373 | B2 * | 4/2006 | de la Torre et al. | 606/191 |

(Continued)

*Primary Examiner* — Gregory Anderson
*Assistant Examiner* — Christopher L Templeton
(74) *Attorney, Agent, or Firm* — Wagenknecht IP Law Group PC

(57) ABSTRACT

The invention relates to an implantation device (10*a-d*) comprising at least one medical implant (12*a-d*) and at least one implantation aid (14*a-d*) comprising at least one expansion element (16*a-d*). It is provided that the expansion element (16*a-d*) can be inserted into at least one cavity (18*a-d*) of the implant (12*a-d*), and the at least one cavity (18*a-d*) can be expanded using the expansion element (16*a-d*), and, in the end state, the expansion element (16*a-d*) is disposed at least partially in the at least one cavity (18*a-d*), wherein the expansion element (16*a-d*) is designed as a solid body (20*a-d*).

14 Claims, 12 Drawing Sheets

(56) References Cited

U.S. PATENT DOCUMENTS

| | | | |
|---|---|---|---|
| 7,101,395 B2* | 9/2006 | Tremulis et al. | 623/2.11 |
| 7,153,323 B1* | 12/2006 | Teoh et al. | 623/1.23 |
| 7,503,930 B2* | 3/2009 | Sharkawy et al. | 623/2.11 |
| 7,695,488 B2* | 4/2010 | Berenstein et al. | 606/194 |
| 8,128,691 B2* | 3/2012 | Keranen | 623/2.37 |
| 2001/0003801 A1* | 6/2001 | Strecker | 623/1.11 |
| 2004/0199175 A1* | 10/2004 | Jaeger et al. | 606/108 |
| 2005/0004669 A1* | 1/2005 | Sievers | 623/2.36 |
| 2006/0004442 A1 | 1/2006 | Spenset et al. | |
| 2006/0009841 A1* | 1/2006 | McGuckin et al. | 623/2.38 |
| 2006/0020334 A1 | 1/2006 | Lashinski et al. | |
| 2006/0276839 A1* | 12/2006 | McGuckin | 606/213 |
| 2007/0233239 A1 | 10/2007 | Navia et al. | |
| 2009/0099592 A1* | 4/2009 | Buiser et al. | 606/200 |
| 2009/0287145 A1 | 11/2009 | Cragg et al. | |
| 2011/0230961 A1* | 9/2011 | Langer et al. | 623/2.27 |

* cited by examiner

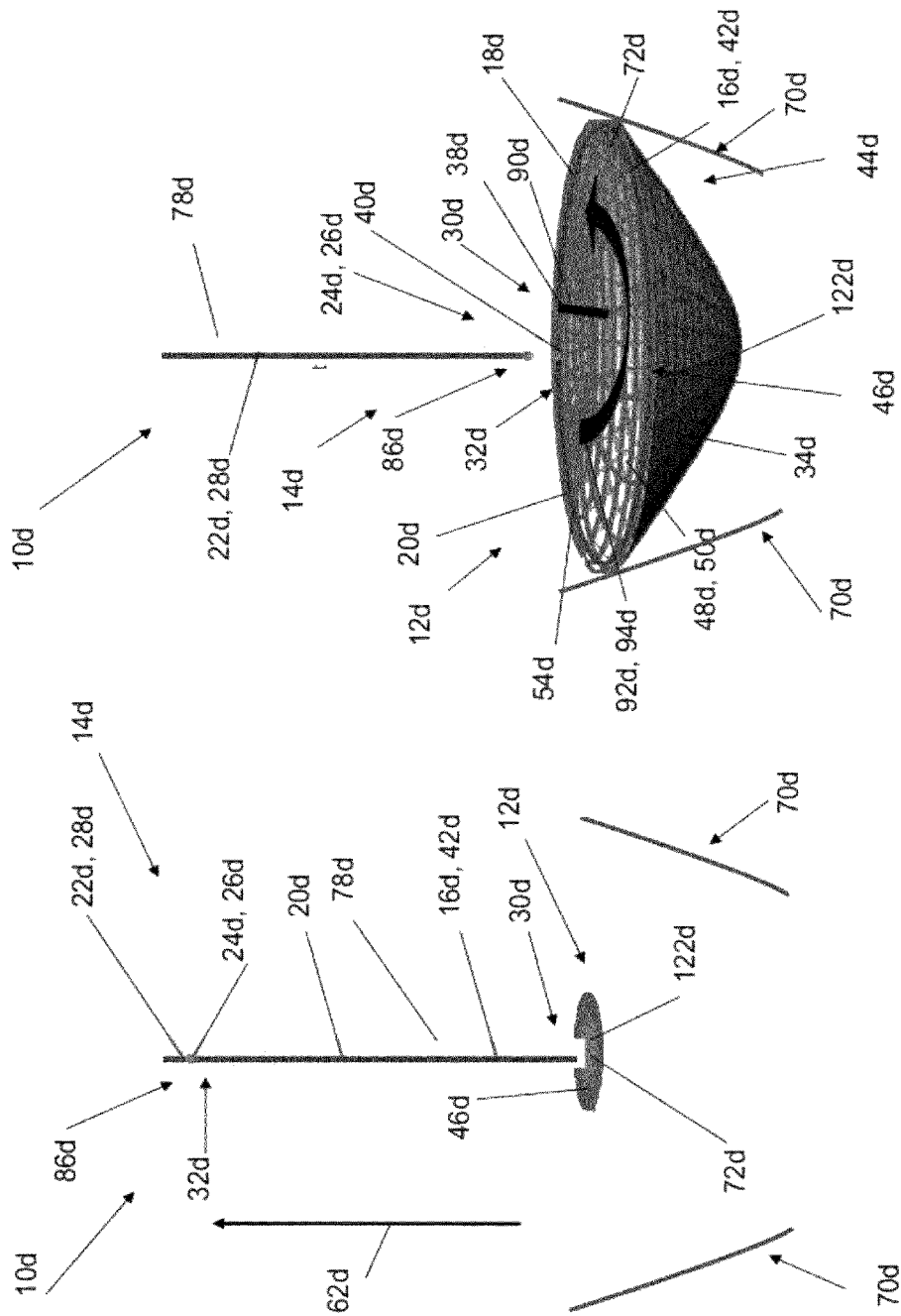

IMPLANTATION DEVICE

CROSS REFERENCE TO RELATED APPLICATIONS

This is a nonprovisional application of U.S. provisional patent application Ser. No. 61/440,425, filed Feb. 8, 2011; the contents of which are herein incorporated by reference in their entirety.

TECHNICAL FIELD

The invention relates to an implantation device an expansion element and a medical device for implantation in an animal body and/or human body.

BACKGROUND

Implants are used in medical applications for implantation in an animal body and/or human body permanently or at least for an extended period of time to perform replacement functions. Heart valve implants are known, for example, such as aortic valve implants that perform the function of the natural aortic valve. In that case, the valve implant is affixed after expansion of the implant structure immediately after implantation, and assumes the position of the natural aortic valve.

SUMMARY

A problem that occurs frequently is that the implant is affixed in an incorrect position, which can cause the implant to fail. This occurs often e.g. with calcification, that is, the deposition of sodium salts, in particular calcium phosphate (hydroxyapatite) on the structures of the heart and, in particular, when an aortic stenosis has calcified in a highly asymmetrical manner. In addition, it is often impossible to change the position of implants once they have been positioned. Furthermore, anchoring mechanisms are often used that may damage the tissue at an implantation site.

The problem addressed by the invention is that of creating an implantation device comprising an implantation aid and an expansion element, and a medical implant which can be used to implant the implant at an implantation site exactly, reliably, in a manner that is gentle to tissue, and such that it can be repositioned.

The problem is solved by an implantation device comprising at least one medical implant and at least one implantation aid comprising at least one expansion element.

It is provided that the expansion element can be introduced into at least one cavity of the implant, and the at least one cavity can be expanded using the expansion element, and, in the intended end state, the expansion element is disposed at least partially in the at least one cavity, wherein the expansion element is designed as a solid body. By way of the embodiment according to the invention an implantation device can be provided that can be used to position the implant in an optimal manner and anchor it in a gentle manner. Furthermore, the implant can therefore be advantageously adapted to the parameters or anatomical details of the particular implantation site, such as the calcification of a blood vessel wall and/or an annulus, and/or another, hereditary and/or diseased anomaly of the implantation site. Moreover, it enables optimal placement at the site of the defective physiological unit, such as a valve. In addition, repositioning and permanent fixation of the implant in vivo are made possible.

In this context, an "implantation device" refers, in particular, to a device such as a catheter system which can be used to place an implant in an animal body and/or human body for temporary or permanent implantation. An "implant" is intended to mean, in particular, a body that performs at least one replacement function permanently, for an extended period of time, or temporarily when implanted in an animal body and/or human body. Any medical implant that appears appropriate to a person skilled in the art would be feasible in this case, such as a cardiac pacemaker, a brain pacemaker, a cardiac implant, a cochlear implant, a retinal implant, a dental implant, a joint replacement implant, a vascular prosthesis, or others. Particularly advantageously, an embodiment of the medical implant is provided as a valve implant. Furthermore, an embodiment as a safety implant is also feasible, which is implanted during surgery e.g. as a retaining means in the region of the surgical intervention.

In this case, an "implantation aid" is a means, in particular, such as a catheter shaft, a cannula or, in particular, a wire and/or a spring that is used as an aid during implantation. In this case, an "expansion element" is intended to mean, in particular, an element that changes the expansion of another element by assuming a certain configuration and/or shape. Expansion takes place in particular by inserting the expansion element into the cavity. As a result and, in particular, when insertion is performed slowly, it is advantageously possible to obtain a good adaptation of the implant to a morphology of the heart. Furthermore, the expansion of the cavity can be reduced once more by retracting the expansion element, thereby providing an easy way to perform repositioning.

In this context, a "cavity" means, in particular, a space that has a recess which is surrounded by an enclosure by at least 90%, preferably by at least 95%, and particularly preferably by at least 98%. In this case, an "intended end state" or "end state" is the implanted state in particular. The expression "at least partially" in this case preferably means more than 50%, particularly advantageously more than 75%, and particularly advantageously more than 95% of the expansion element. Preferably 100% of the expansion element, i.e. the entire element, is disposed in the cavity.

In this context, a "solid body" refers to a body in the solid aggregate state thereof. Preferably the solid body is an elastic solid body, wherein "elastic" is intended to mean that the solid body is reversibly deflectable and/or can assume a configuration in which it has a spring constant. In this case, a solid body does not refer to a gas, liquid, and/or gel in particular. The solid body can be formed of a material such as a polymer, glass, rubber, metal, a ceramic, an alloy, and/or any other material considered reasonable to a person skilled in the art. Furthermore, the solid body can have any design or shape that appears advantageous to a person skilled in the art, such as a linear wire, a spring, and/or a coiled spring, for example.

The invention is furthermore directed to an implantation aid comprising at least one delivery element and at least one expansion element for an implantation device.

It is provided that the implantation aid comprises at least one detachable connection between the at least one delivery element and the at least one expansion element. By way of the embodiment according to the invention, the expansion element can be manipulated using the delivery element repeatedly and even after positioning in the cavity has been carried out, by reconnecting the elements. Furthermore, delivery and insertion of the expansion element into the cavity can be achieved by way of a simple design.

In this context, a "detachable connection" means, in particular, a reversible connection or a connection that is capable of being reversibly opened and closed, or that is reversibly opened or closed. This connection can be designed as any type of connection considered reasonable by a person skilled in the art, such as a threaded connection, a Velcro connection, a plug connection, a rotational connection, a form-fit connection, or a non-positive connection. A "delivery element" in this context refers in particular to an element which is advanced toward the implantation site with the implant during implantation, and/or which is advanced toward the implant that is already located at the implantation site. The delivery element is not implanted. The delivery element and the expansion element are preferably made of the same material. Basically, however, the selection of any materials that appear reasonable to a person skilled in the art is feasible.

A detachable connection that is reliable and structurally simple can be advantageously provided when the detachable connection has a bayonet catch. In that case, rotating the delivery element in the counterclockwise direction establishes a connection or closes the connection between the delivery element and the expansion element. Rotation in the counterclockwise direction about the own axis thereof is also possible, which can advantageously support the advancement of the expansion element into the cavity. Rotation in the clockwise direction opens the connection.

As an alternative, it can be advantageous for clamping jaws for the detachable connection to be disposed on the delivery element, in particular on the distal end thereof. In that case, the expansion element comprises a mating part such as a squared end on the proximal end thereof. In this context, a "proximal end" is intended to mean an end of the support frame that points toward the operator or the physician during the implantation process. Accordingly, a "distal end" is an end that points away from the operator. The clamping jaws can be opened or closed e.g. by rotating the delivery element. A reliable mechanical connection is established as a result, which permits rotational motions and linear motions in both directions.

The delivery element is advantageously formed by an elastic wire. This wire is preferably made of a Ni—Ti alloy, such as Nitinol, medical stainless steel such as the alloy 316L, CoCr alloys MP35N and L605 and/or a Pt/Ir alloy. Basically, however, any other material that appears usable to a person skilled in the art, such as plastic, glass, ceramic, and/or rubber would be feasible. By way of the elastic wire, advancement to the implantation site can be implemented in a manner that is structurally simple and saves space. In addition, for instance, blood flow in a vascular system used during implantation is only minimally disturbed.

The invention is furthermore directed to an expansion element comprising a body for an implantation device, which extends between a distal end and a proximal end.

It is provided that a connecting structure for connection to a fastening means of an implant is disposed on the distal end, and/or a connecting structure for connection to a delivery element of an implantation aid is disposed on the proximal end. A "body" in this case is the expansion element itself in particular. In this context, a "connecting structure" refers in particular to a structure that interconnects two elements permanently or, preferably, reversibly. The connecting structure on the distal end is advantageously designed such that it can be captively connected to a mating part, and is preferably formed by a squared end. The connecting structure on the proximal end enters into a reversible connection in particular and is preferably designed as part of a bayonet catch or squared end that can interact with clamping jaws. Any other type of structure that appears reasonable to a person skilled in the art would also be feasible, however. A connecting structure is preferably disposed at both ends of the expansion element. Detachment from the delivery element can be accomplished in a structurally simple manner by way of the connecting structure on the distal end. By way of the connecting structure on the proximal end, the expansion element can be easily prevented from co-rotating, thereby ensuring that expansion functions reliably and that the implant can be placed and affixed in an exact manner.

In addition, it can be advantageous for the body to be formed by an elastic wire. The wire can be made of the same materials as the wire of the delivery element, and is a metal wire composed of Nitinol in particular. Due to the embodiment as an elastic wire, expansion can be carried out using a simple design. Furthermore, the expansion can be reversed quickly and in an uncomplicated manner by withdrawing the wire, thereby making it easy to reposition the implant. In addition, repositioning can be carried out at any time since the connection to the delivery element can be restored.

According to a preferred development, the body is provided to act as a spring having pronounced radial forces. By advancing the expansion element into the cavity, the wire takes on an elliptical shape due to the guidance thereof on a wall of the cavity. The wire is thereby reversibly reshaped into a spring or annular spring which exerts radial forces and expands the cavity. The implant is thereby fixed in position at the implantation site. The wire can form a plurality of coils in the cavity. Furthermore, the mechanical properties can be adapted to the application by way of the specific design. By employing this annular spring principle and the manner in which the implant is fixed in position, automatic adaptation to anatomical details can be achieved in a simple, advantageous manner.

The invention is furthermore directed to a medical implant for implantation in an animal body and/or human body, comprising a support frame for an implantation device, the support frame comprising at least one element having at least one cavity.

It is provided that the cavity is designed to accommodate an expansion element in the intended end state, and at least one region of the at least one element is designed to be expandable using the expansion element, wherein the expansion element in the intended end state thereof is at least partially located in the at least one cavity and is designed as a solid body. The embodiment according to the invention makes it possible to provide an implant that has good self-positioning properties and therefore undergoes optimal placement. Furthermore, a pressure gradient of the flow medium acting on the medical implant can be kept homogeneous, which advantageously results in a minimal material load on valve implants, for example, and, therefore, in a minimal risk of fatigue since the valve opens in a uniform manner. In turn, this results in a long service life of the cusp and, therefore, the valve. Furthermore, better clinical results compared to conventional valve implants can be achieved by the improved functionality of the valve that can therefore withstand a higher pressure gradient in the presence of an asymmetrically calcified annulus. Due to the embodiment according to the invention, symmetry in the flow dynamics of the flow medium can be increased, which advantageously reduces the risk of further calcification. Furthermore, the implant is optimized in terms of flow mechanics, thereby making it possible to reduce turbulent flows of the flow medium, which, in turn, reduces the tendency for clots to form.

Furthermore, a "support frame" in this context is intended to mean, in particular, a structure that substantially imparts a shape and/or form to the implant. The support frame preferably comprises at least one ring or a hollow ring and/or a hollow cylinder, such as a tubular polymer cylinder, for example. The element can be formed by the support frame itself, or can be only a portion of the support frame. The region of the element can be the cavity itself and/or the wall or enclosure thereof. In a supportive manner, the implant can be expandable or can be expanded using a force applied from the outside, or can be plastically deformable. The passive expansion can be accomplished in a structurally simple manner using a balloon catheter, wherein the implant can be crimped onto a balloon catheter.

It is furthermore provided that the implant includes at least one guide means. The term "guide means" is intended to mean, in particular, a means that influences and/or determines a direction of motion, a route, an orientation, and/or an arrangement of the expansion element by way of one of its parameters, such as orientation, shape and/or arrangement. Advantageously the guide means is provided to guide the expansion element tangentially during insertion and/or expansion of the region, thereby making it possible to minimize the feed forces. By way of the guide means, it is advantageously possible to predetermine and therefore influence a motion of the expansion element.

Furthermore, the guide means are advantageously disposed on a proximal end of a structure of the implant such as the support frame, thereby enabling good accessibility of the expansion element upon insertion into the cavity and/or of the delivery element upon contacting the expansion element. Advantageously in terms of finding the way, the guide means are located directly at an entrance, such as a recess, to the cavity. The entrance or recess can comprise a closing means that is overcome when the expansion element is inserted. Furthermore, it is advantageous that air can be prevented from escaping from the cavity, for example, and/or that blood can be prevented from entering the cavity by providing a valve, for instance, as the closing means in the recess, thereby preventing an unwanted exchange of media. It can also be advantageous if, in the intended end state, the recess can be closed by an exact-fit seat of the proximal end of the expansion element, thereby making it possible to omit a separate closing means and reduce the number of components required. In general it would also be possible for the proximal end to extend beyond an outer surface of the support frame. Particularly preferably the guide means are formed by a funnel. According to an alternative embodiment, the guide means or funnel can be disposed on the distal end of the delivery element, thereby preventing turbulence from forming in the blood in the implanted state of the guide means, which are now not present. As an alternative, the funnel may also be subsequently removed from the implant, e.g. in a follow-up examination, which is minimally invasive.

Advantageously, the expansion element can be anchored well with strong holding force when the implant comprises at least one fastening means. The fastening means is advantageously disposed in the at least one cavity and preferably on one end of the route of the expansion element, which is predetermined by the guide means, thereby ensuring that the cavity can be expanded using the expansion element in a controlled manner. The fastening means is preferably disposed in a wall, the plane of which extends substantially perpendicularly or perpendicularly to the direction of motion or direction of advancement of the expansion element. To permit the expansion element to form a plurality of coils in the cavity, this wall can comprise recesses for passage of the expansion element. Furthermore, the fastening means are provided to affix the expansion element at least in the intended end state. Particularly good fixation can be ensured and the expansion element with the delivery element can be prevented from co-rotating when the fastening means is designed as a mating part to a squared end. In general, however, any other type of fastening means that appears reasonable to a person skilled in the art would also be feasible.

According to a further embodiment of the invention, the support frame comprises at least one positioning means. The positioning means can form the entire support frame or can be only a portion of the support frame. The positioning means can therefore be a thickened region, a ridge, and/or an annular structure which is integrally formed with the support frame and/or is formed therein. Basically the positioning means can also be connected to the support frame in another way, such as a non-positive connection, a bonded connection, or a form-fit connection. The positioning means is used in particular to support fixation of the implant, thereby making it advantageously possible to omit e.g. thorn-like anchoring mechanisms according to the prior art, which irritate the tissue and can induce inflammation. The positioning means can also be used to position the implant exactly. The positioning means is also a means for mechanically reinforcing the structure of the implant.

According to a further embodiment of the invention, the element of the support frame and/or the positioning means is formed by at least one annular structure, thereby enabling the implant to be placed and affixed at the annulus in a physiologically optimal manner by way of self-positioning. In this case as well, the element or the annular structure can form the entire support frame or can be only a portion of the support frame. The annular structure can be formed by a hollow ring, wherein the wall or enclosure of the ring is designed to be expanded by the expansion element and/or to guide the expansion element during expansion. The enclosure is made of a flexible polymer material in particular, preferably such as polyethylene (PET), polycarbonate (PC), polyvinyl chloride (PVC), polyimide (PI), PEBAX, PVP, PA11. In principle, however, it may be made of any material that appears usable to a person skilled in the art. If the implant is made of polymer, the design thereof can be extremely flexible. Furthermore, a small implantation diameter can be obtained since no metal or only a small quantity of metal is located in the catheter at the time of implantation. Furthermore, since there is no direct contact of metal with the cardiac wall, a disruption of the propagation of electrical pulses on the heart can be prevented.

Advantageously, the medical implant comprises at least two annular structures, thereby enabling placement and self-positioning at the implantation site, such as the annulus, to take place in a particularly exact manner. An exact and secure fixation can be advantageously achieved when the annular structure is disposed on a proximal end and/or a distal end of the support frame. Preferably an annular structure is disposed on the proximal end as well as on the distal end, thereby enabling the shape of the support frame to be adapted in a particularly reliable manner to the shape of the implantation site or the annulus. This also makes it possible to obtain a comfortable, short installation height of the implant or the valve implant, thereby minimizing hazards such as blocking or closing the entrances to the coronary arteries.

If the two annular structures can be expanded independently of one another, the implant can be positioned in a particularly precise manner. In that particular case, the distal ring is expanded first, thereby forming a stop for the optimal positioning of the implant, e.g. in the form of an artificial aortic valve. Once the distal ring has been placed correctly, the proximal ring is expanded and the implant or the heart valve is centered automatically in the region of the constriction formed by the defective physiological heart valve. Repositioning can be carried out by withdrawing the wires.

It is also provided that the annular structure can be filled with a curable material, thereby enabling permanent fixation to be easily supported. The curable material can be liquid or viscous in the filling state. In this context, "curable" is intended to mean, in particular, that a material used for filling transitions from a first, liquid, or less viscous state into a second, more viscous, preferably solid state. The state transition can be dependent upon any physical, chemical, or electrical factor that appears reasonable to a person skilled in the art, such as time, temperature, radiation (IR, VIS, UV, gamma, radioactive radiation), ultrasound, magnetism, current, or a change in pH value, concentration, and/or charge. The material is advantageously more highly polymerized and/or crosslinked. Advantageously a crosslinkable polymer solution is used. Preferably the polymer solution can be composed of a plurality of components, the relative ratio and composition of which advantageously makes it possible to set physical properties. Optionally, different properties of the individual annular structures can also be implemented. Advantageously, the reaction speed can be influenced directly by the ratio of polymeric to monomeric portions and the concentration of chemically active substances (initiators for the polymerization). Advantageously the curable material is selected from a group composed of: acrylates, methacrylates, cyanoacrylates, epoxides, urethanes, acrylamides, acyl acids.

It is also provided that at least one connecting structure is located between two annular structures. In this context, a "connecting structure" refers in particular to a structure that mechanically interconnects the two annular structures. It is preferably formed of a continuous polymer foil that insulates the defective human valves against the new, usually animal-based valve material of the implant, thereby minimizing a contact surface between the artificial valve and an aortic wall in a manner that is gentle to tissue. Furthermore, calcification of the animal-based valve material can be effectively prevented in this manner, which could jump to the animal-based valves if there were direct contact with the defective human valves.

It is furthermore provided that the support frame comprises a stent and/or the connecting structure forms a stent. For this purpose, the polymer of the connecting structure can be made of a curable material. It is preferably curable using the same mechanism as the material used to fill the annular structure. Given that the support frame comprises a stent, positioning of the implant and/or adaptation to anatomical details at the implantation site can be further supported.

If the implant comprises a valve that is disposed proximally in an axial direction above the annular structure on a proximal end of the support frame, a smaller implantation diameter can be utilized, which is advantageous. In that particular case, the valve is preferably attached to the proximal annular structure. Basically the valve can also be disposed axially between two annular structures, however. This results in a particularly reliable adjustment of the valve. When positioning between the annular structures, the valve can also be installed on the connecting structure and/or connected to an annular structure or to both annular structures. The valve can be connected to the annular structure or the support frame using any type of connection deemed to be reasonable to a person skilled in the art, such as suturing and/or bonding.

According to a further embodiment of the invention, a support structure is disposed on at least one annular structure, on the proximal end of the support frame and/or on the proximal end of a valve. This support structure is preferably used to support, position, and provide proximal mechanical fixation of the valve. It is preferably designed as a metal framework in the form of a wire mesh, preferably of Nitinol, and/or as a further or third annular structure which can be positioned, expanded, and affixed independently of the other functional units of the implant. By way of the support structure, the relative positioning of the annular structures and the valve cusps can be ensured, to guarantee that the cusps open and/or close exactly and without complication. The embodiment as a further annular structure is advantageous in particular when this annular structure has high mechanical flexibility and therefore enables good adaptation to the physiological details of the heart. As a result, optimal flow properties and low mechanical restriction of heart motion can be achieved.

According to a preferred development, at least two annular structures in the intended end state are disposed axially in front of and behind an annulus in the direction of flow of a flow medium. In this context, a "flow direction of a flow medium" refers, in particular, to the scientifically known flow direction of arterial and/or venous blood in the heart and, particularly advantageously in the case of the aortic valve, to the flow of blood from the left ventricle into the aorta. The annulus is preferably the aortic annulus. Due to the implementation of the embodiment according to the invention, the implant can be adapted particularly well to the anatomy of the heart or a heart valve region e.g. with an aortic bulb.

Furthermore, it is advantageous if the support frame and/or the connecting structure are provided to compensate for a difference in a shape of an inner cross section of the support frame and/or connecting structure and a cross-sectional area of an implantation site. "Provided" is intended to mean, in particular, specially equipped, designed, and/or prepared. In this context, a "shape of the inner cross section of the support frame" refers, in particular, to a largely round or cylindrical shape which enables the cusp of the valve to open and close without complication. A "cross-sectional area of the implantation site" in this context is intended to mean, in particular, a highly asymmetrical or non-circular site, in particular having a calcified aortic stenosis. The support frame thereby advantageously adapts the possible non-uniform shape of an outer diameter of the support frame to the cross-sectional area of the implantation site, thereby enabling the implant to take particular account of the local details at the implantation site. Advantageously as a result, an asymmetry of the blood vessel wall or the annulus can be compensated for, and a largely round, symmetrical inner shape of the support frame can be retained nevertheless to ensure the required flawless, complication-free function of cusps of the valve.

According to an advantageous development, the implant is designed as a protective structure. In this context, a "protective structure" refers in particular to a structure that is implanted temporarily, i.e. for the duration of a medical procedure, for example, and/or that can perform a protective function during a medical procedure. The protective structure is preferably designed as a retaining means. For this purpose, a shield formed by a polymeric web is disposed on the annular support frame thereof, preferably on the distal end thereof. In general, the shield or web can also be made of any other material considered usable by a person skilled in the art, such as metal, rubber, or ceramic. By way of the embodiment as protective structure in combination with the annular spring principle of reversible expansion, an implant can be provided that can be implanted quickly, securely, and in a manner that is gentle on tissue, but which can also be explanted without complication.

An embodiment of the implant as a valve implant is advantageous. In this context, a "valve implant" is intended to mean a body in particular that performs at least one replacement function for a non-return valve, permanently or for an extended period of time after implantation. Any medical valve implant that appears suitable to a person skilled in the art, and that is implanted in a cavity of the body, such as a digestive tract, a bronchial tract, and/or a blood vessel, such as an artery and/or vein, would be feasible in this context. The valve implant is preferably a heart valve implant having a valve composed of natural and/or synthetic material.

A preferred development is an embodiment of the implant as an aortic valve, thereby making it possible to provide a refined replacement structure for the heart valve that malfunctions most often. Favorably, complications such as disruptions of the mitral valve or the need for a cardiac pacemaker can also be reduced. An embodiment as a pulmonary valve, tricuspid valve, or a mitral valve is likewise feasible.

Advantageously, a deposit-inhibiting, in particular calcification-inhibiting coating can be provided on the implant, in particular homocysteinic acid. The risk of a disruption or malfunction of the valve implant can therefore be reduced.

DESCRIPTION OF THE DRAWINGS

The invention is explained in the following in greater detail as an example, with reference to an embodiment depicted in drawings. In the drawings:

FIG. 12A shows an implantation device during implantation of a fourth alternative implant, in a schematic depiction, and FIG. 12B shows the implantation device in FIG. 12A during expansion of a cavity of the implant in FIG. 12A, in a schematic depiction.

DETAILED DESCRIPTION

Figure 1:
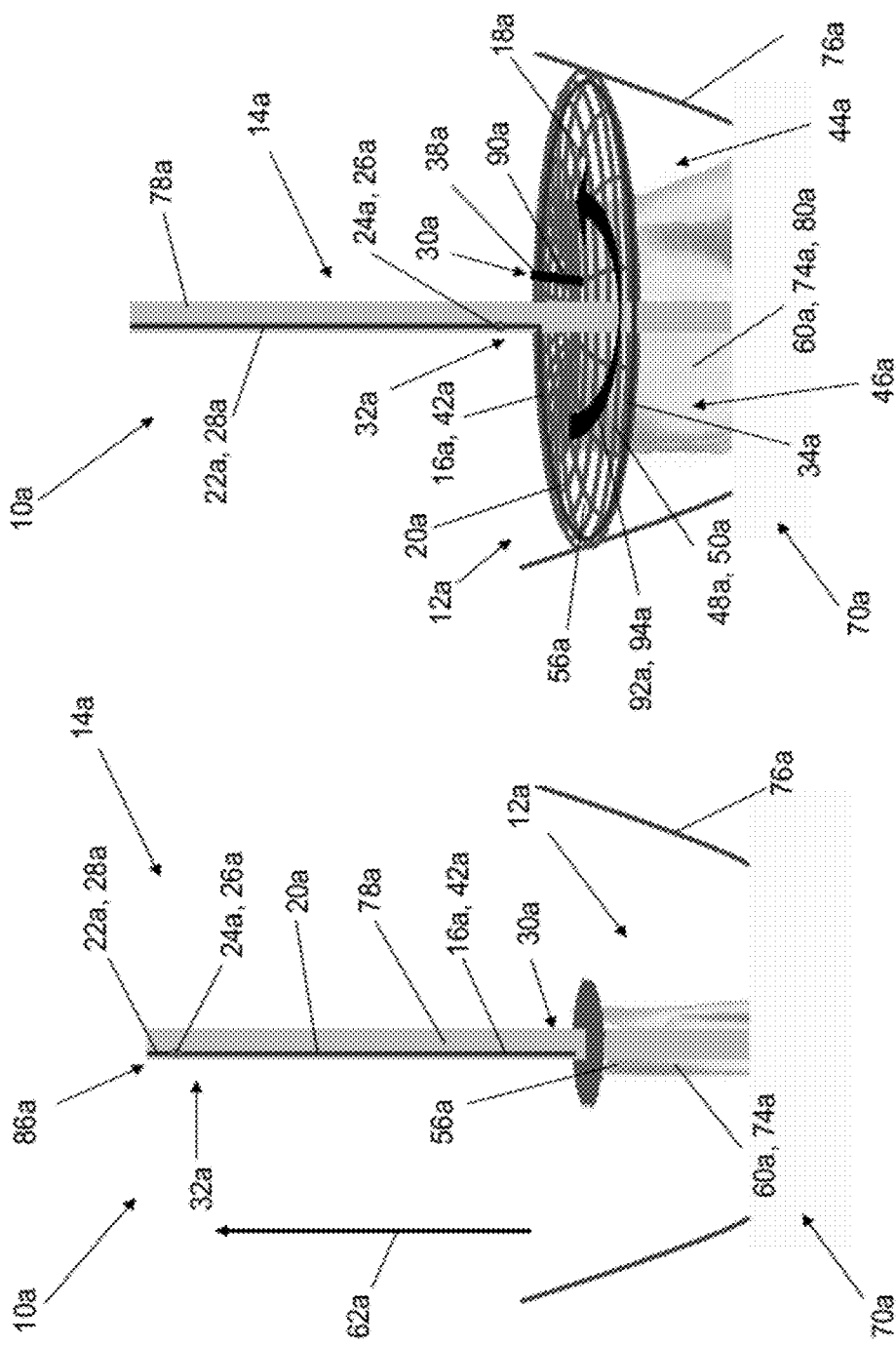
FIG. 1A shows an implantation device according to the invention during implantation, in a schematic depiction.
FIG. 1B shows the implantation device in FIG. 1A during expansion of a cavity of an implant, in a schematic depiction.

Elements that are functionally identical or similar-acting are labeled using the same reference characters in the figures. The figures are schematic depictions of the invention. They do not depict specific parameters of the invention. Furthermore, the figures merely show typical embodiments of the invention and are not intended to limit the invention to the embodiments shown.

Regarding elements in a figure that are not described in detail, reference is made to the corresponding description of the elements in preceding figures to avoid unnecessary repetition.

FIG. 1A shows an implantation device 10a comprising a medical implant 12a for implantation in an animal body and/or human body, and an implantation aid 14a. When implant 12a is implanted at an implantation site 70a, such as an annulus 76a or an aortic annulus, implantation device 10a is advanced to implantation site 70a using a catheter system 78a in a manner known to a person skilled in the art (see FIG. 5). Implant 12a, which is formed by a valve implant 80a and functions in the implanted state as an artificial valve 60a or aortic valve 74a, is in a collapsed state. Implant 12a is expanded using implantation aid 14a disposed in catheter system 78a. For this purpose, implantation aid 14a comprises a delivery element 22a and an expansion element 16a. Expansion element 16a comprises a body 34a which extends between a distal end 30a and a proximal end 32a of expansion element 16a. Delivery element 22a and expansion element 16a or body 34a are both designed as solid bodies 20a or an elastic wire 28a, 42a, or an elastic metal wire composed of Nitinol.

As shown in FIG. 1B, expansion element 16a is inserted into a cavity 18a of implant 12a using delivery element 22a during implantation, wherein cavity 18a is designed to accommodate expansion element 16a in the intended end state which is the implanted state. Cavity 18a is located in an element 48a of a support frame 46a of implant 12a. Element 48a of support frame 46a is formed by an annular structure 56a in the form of a hollow ring. A region 50a or a wall or enclosure 82a of element 48a/annular structure 56a is made of a polymer such as PET and guides expansion element 16a during the expansion thereof. When expansion element 16a is inserted into cavity 18a, wire 42a takes on an elliptical shape due to the guidance in annular structure 56a. Wire 42a or body 34a is thereby reshaped, in a reversible manner, into a spring 44a or an annular spring which exerts pronounced radial forces and expands annular structure 56a or region 50a or enclosure 82a. Cavity 18a is expanded as a result. By way of the expansion, annular structure 56a is affixed to a wall of the heart or a vessel, with automatic adaptation to anatomical details. Optionally, cavity 18a can also have a design that prescribes a partial overlap of the two ends 30a, 32a of expansion element 16a at a close distance to one another. As a result, it is practically possible to define an annular shape during final fixation. Furthermore, by withdrawing wire 42a, the fixation can be reversibly detached and implant 12a can be repositioned at any time.

Once implant 12a has been affixed in the correct position at implantation site 70a, catheter system 78a is withdrawn. Implantation aid 14a has a mechanical detachable connection 24a between delivery element 22a and expansion element 16a. Expansion element 16a remains in cavity 18a, and therefore expansion element 16a is disposed in cavity 18a in the intended end state.

Figure 2:
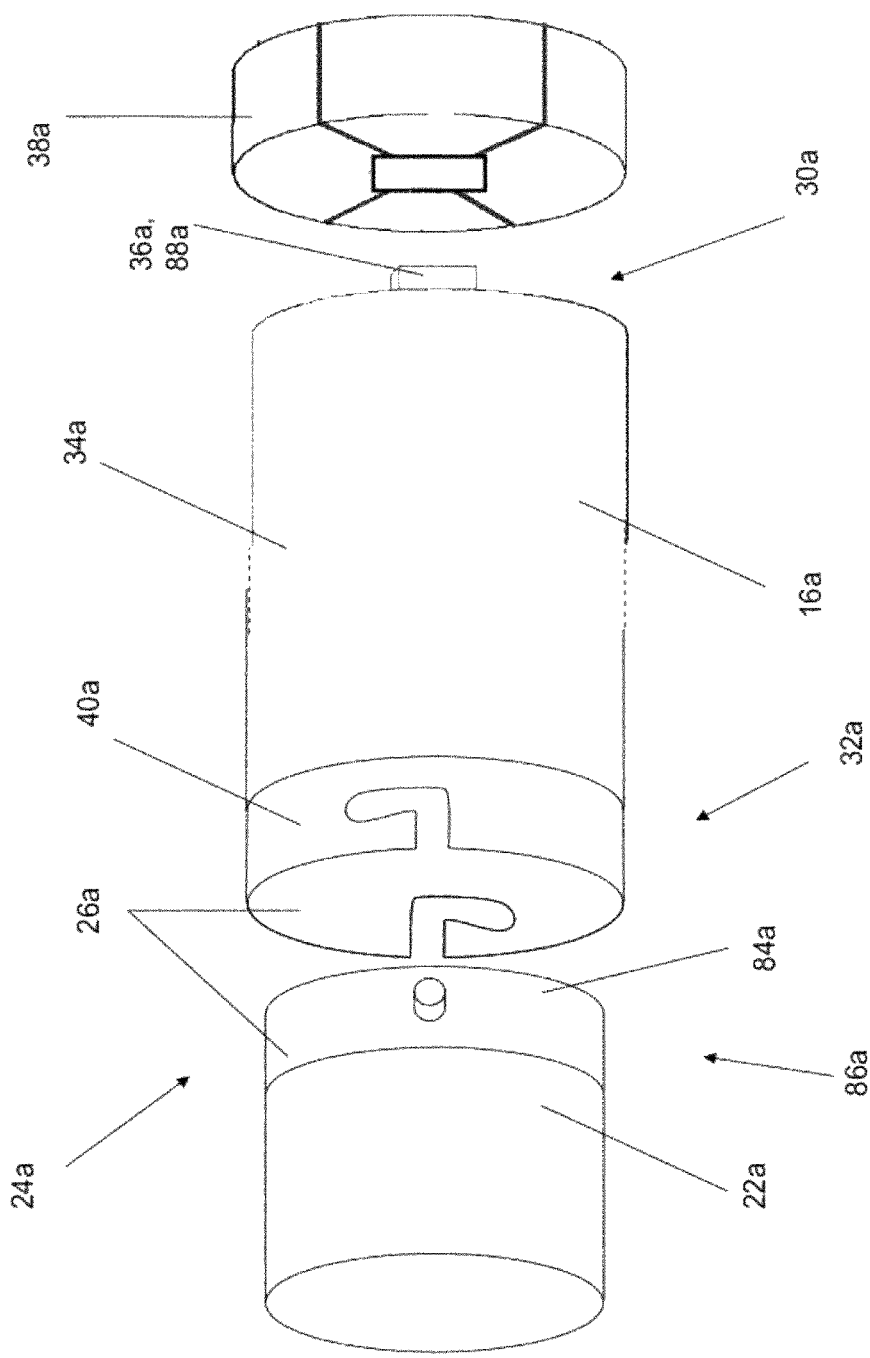
FIG. 2 shows a detachable connection between a delivery element and an expansion element, which is designed as a bayonet catch.

Detachable connection 24a is shown in greater detail in FIG. 2. It comprises a bayonet catch 26a formed by a connecting structure 84a of delivery element 22a on distal end 86a thereof, and a connecting structure 40a of expansion element 16a on proximal end 32a thereof. If delivery element 22a is rotated in the counterclockwise direction, connection 24a can be closed, thereby enabling expansion element 16a to be manipulated. Rotation in the counterclockwise direction about the own axis thereof is also possible, thereby supporting advancement. When rotated in the clockwise direction, connection 24a can be opened after implant 12a has been placed correctly, and delivery element 22a can be withdrawn.

As shown on the left in FIG. 2, expansion element 16a or body 34a comprises on distal end 30a thereof a connecting structure 36a for connection to a fastening means 38a of a implant 12a. Connecting structure 36a is designed as squared end 88a and can be anchored—after the necessary expansion and good placement of implant 12a at implantation site 70a—in fastening means 38a which is designed as the mating part to squared end 88a. Fastening means 38a is disposed in a wall 90a at the end of cavity 18a (see FIG. 1B). A plane of wall 90a extends perpendicularly to a circumferential direction 92a of annular structure 56a. Wall 90a is disposed on a side of the delivery region of expansion element 16a oriented opposite to advancing direction 94a of expansion element 16a. By way of this embodiment, expansion element 16a forms a nearly closed ring that extends around at least 360° after fixation in fastening means 38a or in the implanted state.

Figure 3:
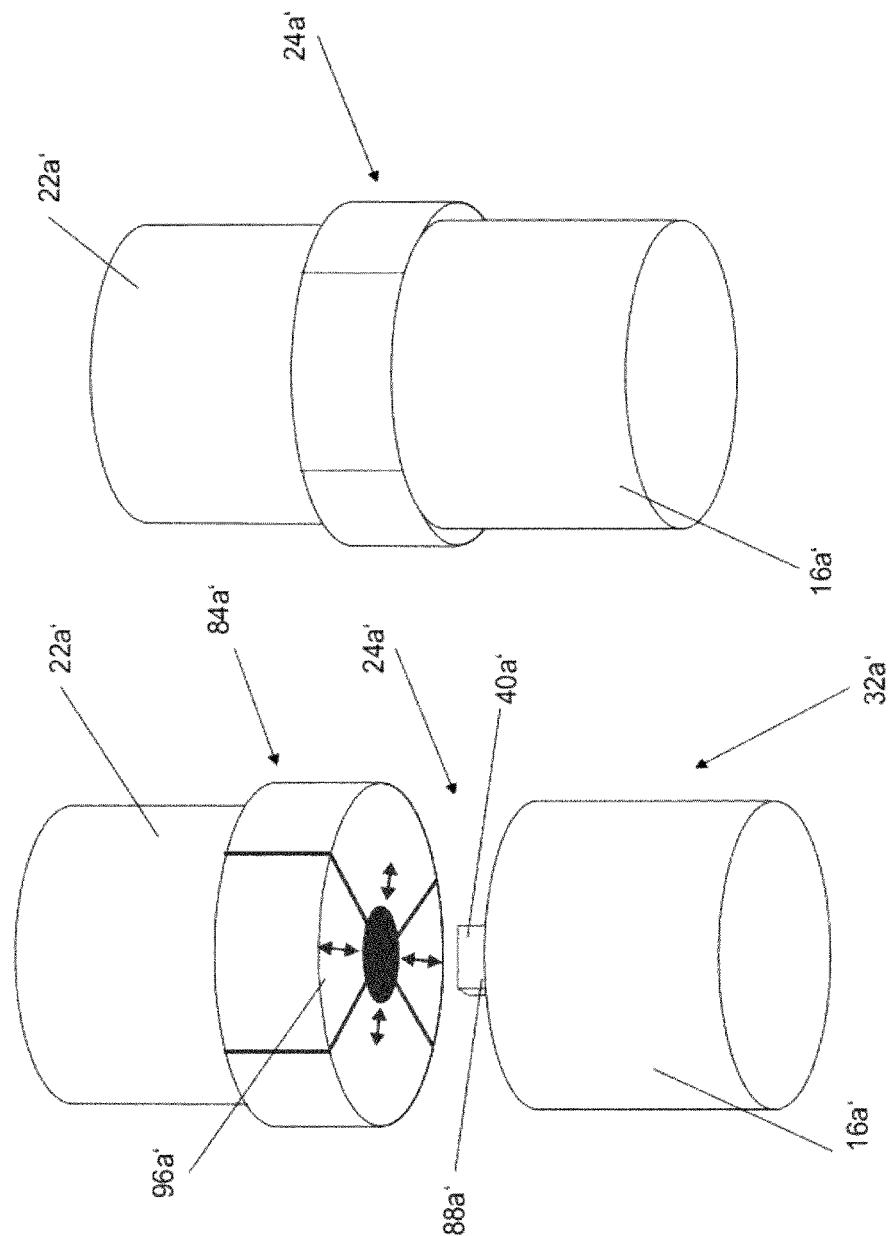
FIG. 3A shows an alternative detachable connection between a delivery element and an expansion element comprising clamping jaws and a squared end.
FIG. 3B shows the connection in FIG. 3A in a closed state.

An alternative embodiment of detachable connection 24a is shown in FIGS. 3A and 3B. Components, features, and functions that are essentially the same are labeled using the same reference characters. To differentiate the embodiments, however, an apostrophe is appended to the reference characters used for the embodiment in FIGS. 3A, 3B. The description below is limited essentially to the differences from the embodiment in FIGS. 1 and 2. With regard for the components, features, and functions that remain the same, reference is made to the description of the embodiment in FIGS. 1 and 2.

FIG. 3A shows an alternative embodiment of a reversible or detachable mechanical connection 24a' between a delivery element 22a' and an expansion element 16a'. A proximal end 32a' of expansion element 16a' comprises a squared end 88a' as connecting structure 40a'. Clamping jaws 96a', which are adapted thereto, are disposed on a distal end 86a' of delivery element 22a' as connecting structure 84a'. They can be opened and closed by way of the rotational motion of delivery element 22a' (see FIG. 3B).

Figure 4:
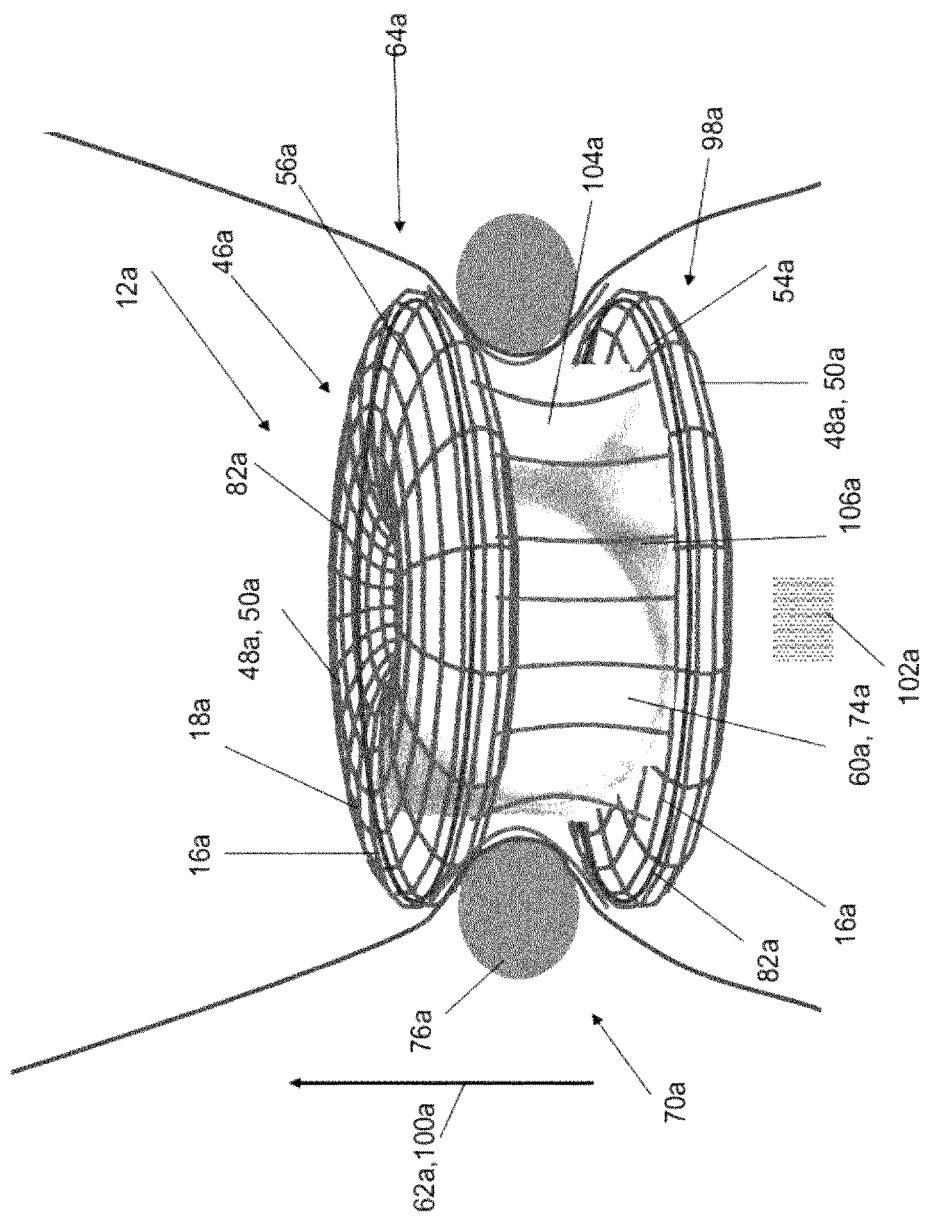
FIG. 4 shows the implant in the implanted state at an annulus, in a schematic depiction.

FIG. 4 shows entire implant 12a after implantation thereof at implantation site 70a or at annulus 76a. Implant 12a comprises two annular structures 54a, 56a disposed on a distal end 98a and a proximal end 64a of support frame 46a, respectively. Annular structures 54a, 56a can be expanded independently of one another using an expansion element 16a. Distal annular structure 54a is expanded first and positioned in an optimal manner using the appropriate mechanism in catheter system 78a. Once distal annular structure 54a has been seated correctly, proximal annular structure 56a is expanded and positioned in an analogous manner, thereby affixing/repositioning percutaneous aortic valve 74a in a reversible manner. Annular structures 54a, 56a are therefore used as positioning means. To provide permanent fixation, annular structures 54a, 56a can be filled with a curable material such as a polymer solution.

In the intended end state, i.e. the implanted state, annular structures 54a, 56a are disposed upstream and downstream of annulus 76a in flow direction 100a of a flow medium 102a, such as blood, in an axial direction 62a. Valve 60a, which comprises cusps 104a made of natural, animal-based material, is placed between annular structures 54a, 56a in axial direction 62a. This embodiment enables a short installation height of support frame 46a to be utilized, thereby ensuring that outlets of the coronary arteries are not covered (not shown).

Support frame 46a also comprises a connecting structure 106a which is designed as a hollow cylinder or a continuous polymer foil and interconnects the two annular structures 54a, 56a. Furthermore, connecting structure 106a rests against annulus 76a or the defective physiological valve in circumferential direction 92a, thereby preventing contact between the diseased valve and implanted valve 60a. The polymer foil of connecting structure 106a can be made of a curable material, and so connecting structure 106a can form a stent in the cured and implanted state.

Figure 5:
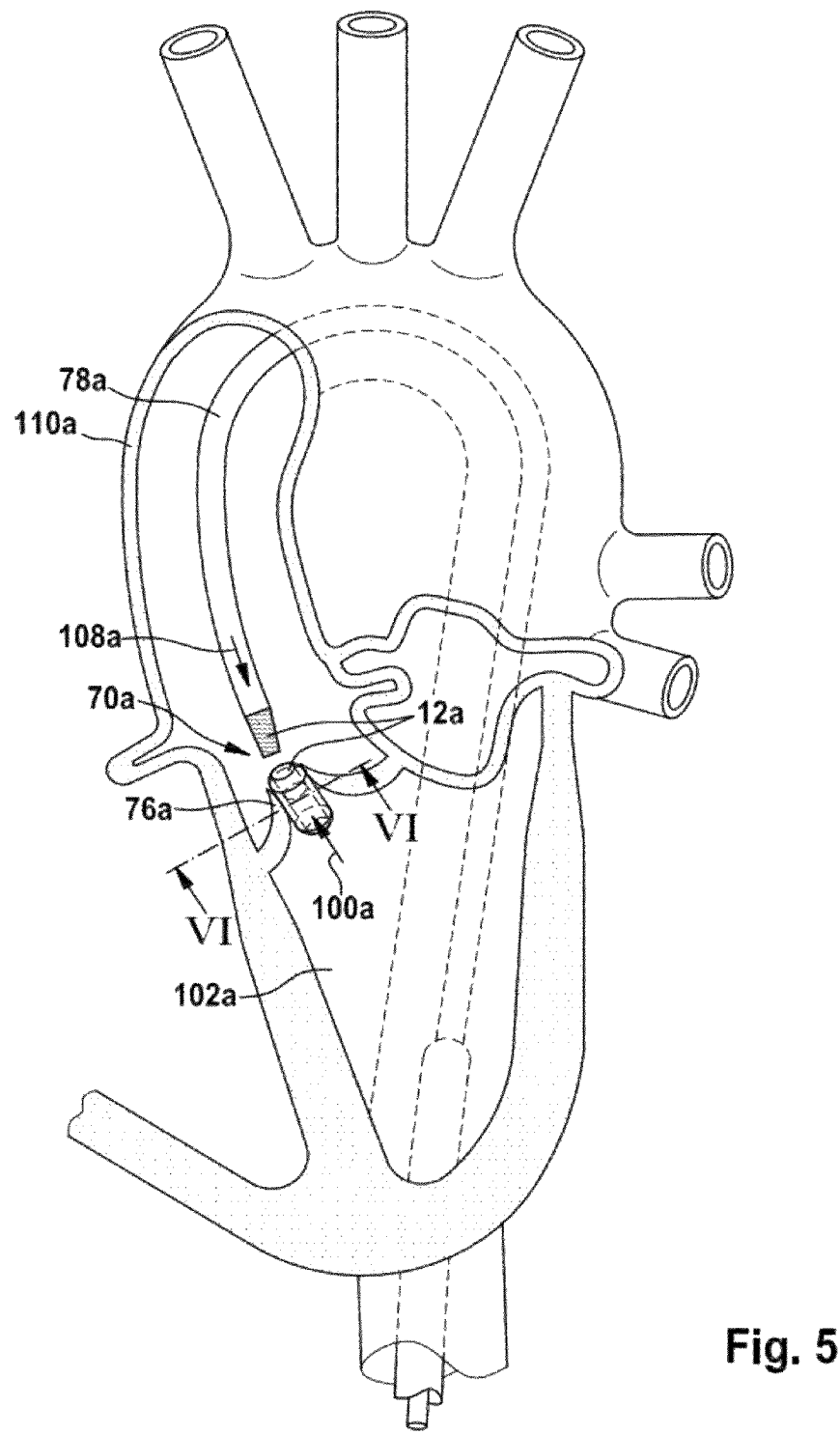
FIG. 5 shows a schematic depiction of the advancement of the implant device in FIG. 1 comprising the implant at an implantation site.

The advancement of implant 12a is illustrated schematically in a partial sectional view in FIG. 5. Implantation device 10a with implant 12a are advanced to implantation site 70a, e.g. annulus 76a of the natural aortic valve with cusps, in a manner known per se. In that particular case, an implantation direction 108a is opposite flow direction 100a of flow medium 102a. Implanted implant 12a is indicated using a dashed line.

Figure 6:
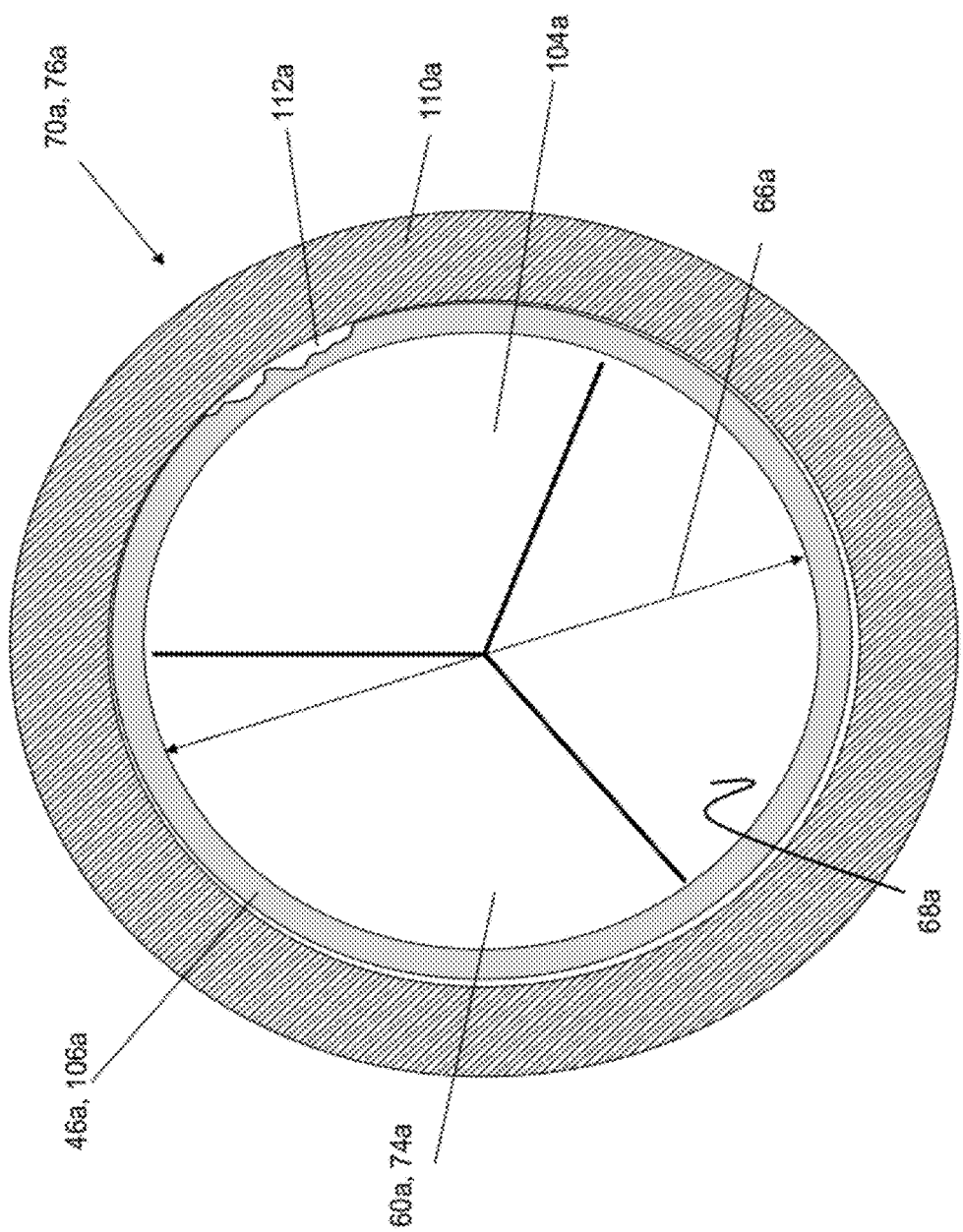
FIG. 6 shows a schematic depiction of a cut along the line V-V in FIG. 5 through an aortic wall, in a top view of the cusp of the valve implant.

As shown in FIG. 6, which is a cut along line VI-VI in FIG. 5 through an aortic wall 110a with a top view of cusp 104a of valve 60a, support frame 46a is provided to compensate for a difference in a shape, in particular a round shape of an inner cross-section 66a of support frame 46a and an e.g. irregular cross-sectional area 68a of implantation site 70a. In the region of a calcification 112a on aortic wall 110a, support frame 46a can adapt to the contour of calcification 112a during implantation, due to flexible and deformable wall 16a thereof, without a round geometry of valve 60a being affected. As a result, cusps 104a can open and close freely. This adaptation can take place in an analogous manner in the region of annular structures 54a, 56a.

Figure 7:
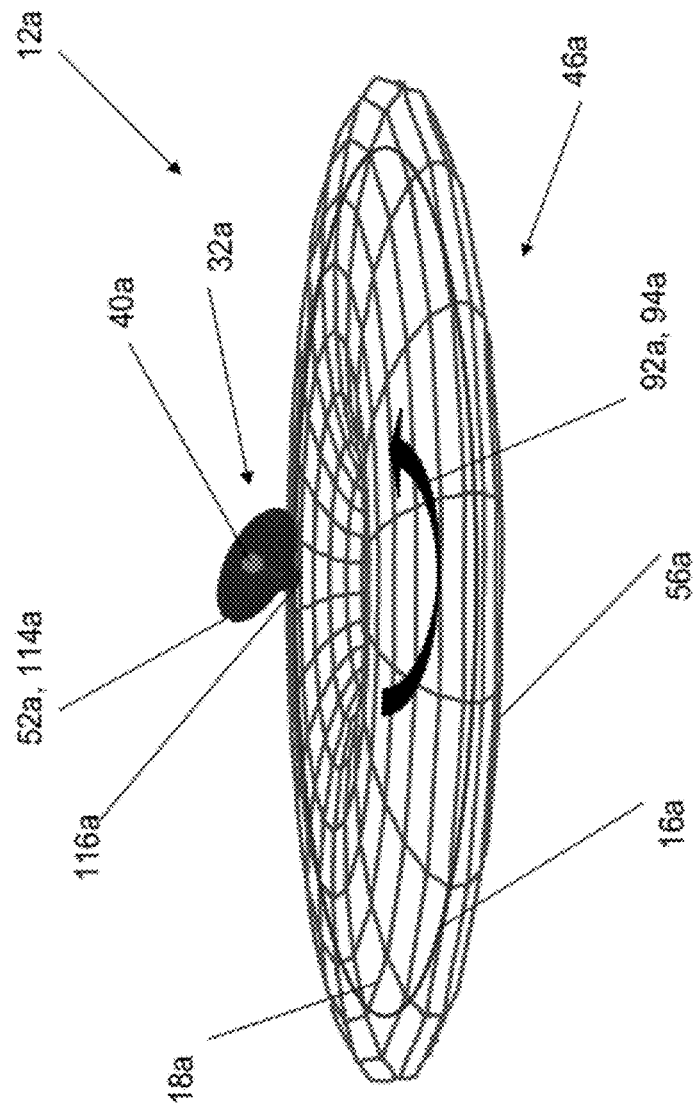
FIG. 7 shows an annular structure of the implant in FIG. 4 comprising a guide means.

FIG. 7 shows a guide means 52a which is provided to tangentially guide expansion element 16a during insertion and/or expansion of region 50a. In that particular case, an orientation or shape of guide means 52a determines the direction, i.e. advancing direction 94a, in which expansion element 16a is moved or directed. Guide means 52a is formed by a funnel 114a and is disposed on a proximal end of particular annular structure 54a, 56a (only annular structure 56a is shown here). Annular structure 56a comprises a recess 116a for insertion into cavity 18a. In the implanted state, proximal end 32a of expansion element 16a extends, by way of connecting structure 40a thereof, out of guide structure 52a and thereby closes recess 116a (not shown true to scale).

Figure 8:
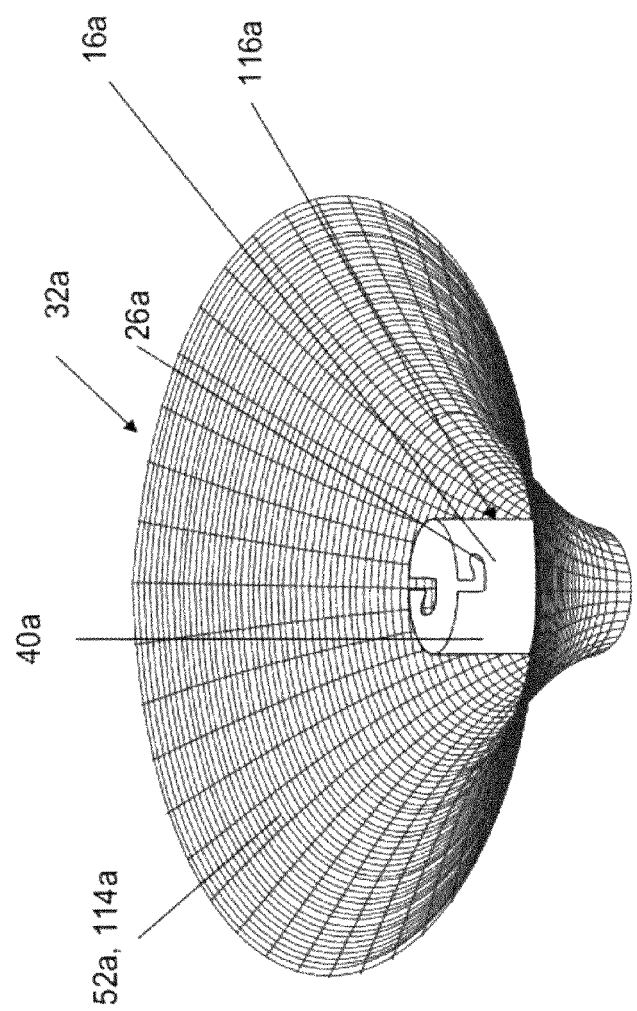
FIG. 8 shows an enlarged depiction of the guide means in FIG. 7 with the bayonet catch of the expansion element.

FIG. 8 shows an enlarged depiction of the arrangement of guide means 52a and expansion element 16a in the inserted state of expansion element 16a. After implantation, bayonet catch 26a of expansion element 16a closes recess 116a. (Funnel 114a is not shown true to scale here.)

Alternative embodiments of implant 12a are shown in FIGS. 9 to 12. Components, features, and functions that are essentially the same are labeled using the same reference characters. To distinguish the exemplary embodiments from each other, the reference characters of the exemplary embodiments are appended with the letters a through d. The description that follows is limited mainly to the differences from the embodiment presented in FIGS. 1 through 8, and reference is made to the description of the embodiment shown in FIGS. 1 through 8 with regard for the components, features, and functions that remain the same.

Figure 9:
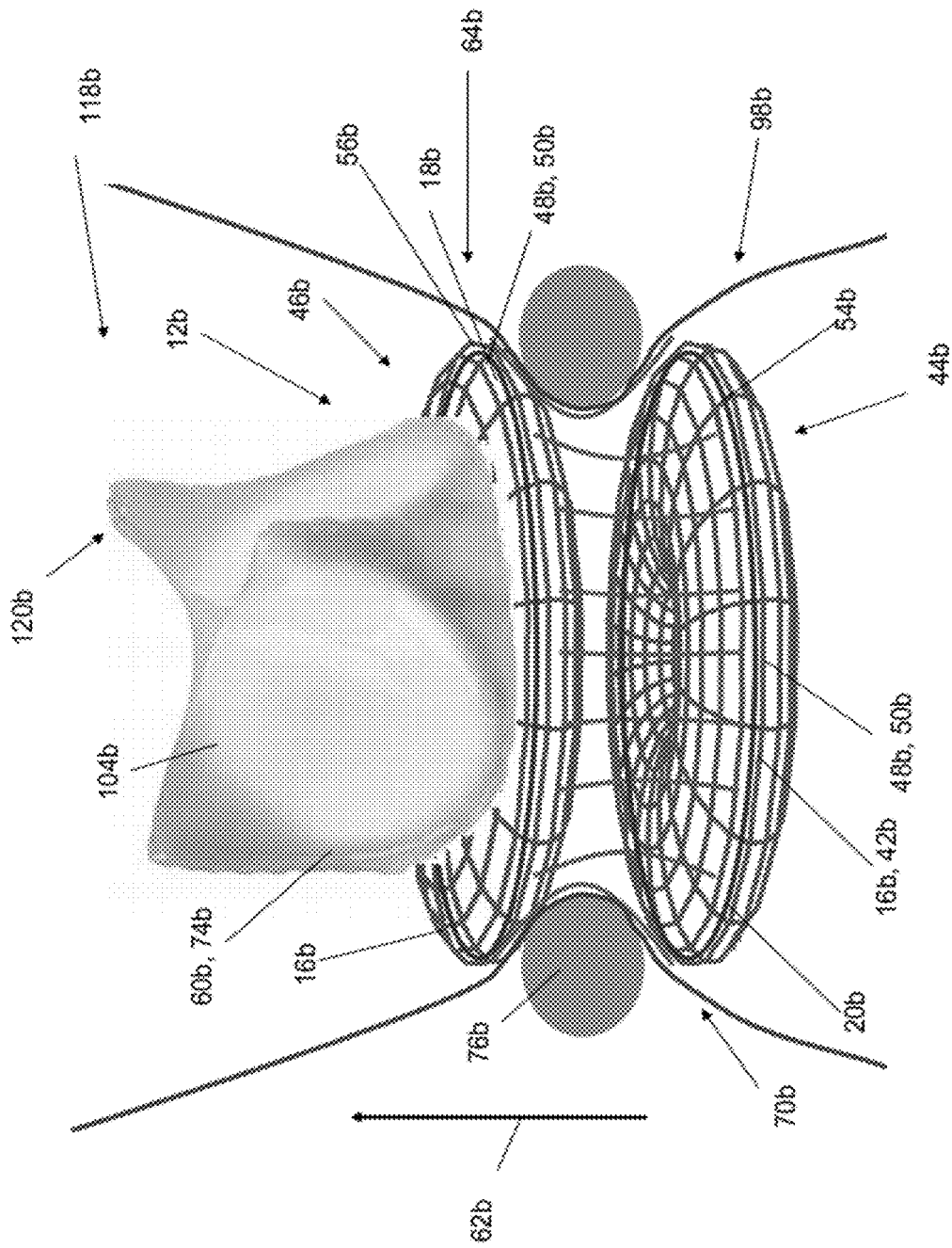
FIG. 9 shows an alternative implant in the implanted state at an annulus, in a schematic depiction.
Figure 10:
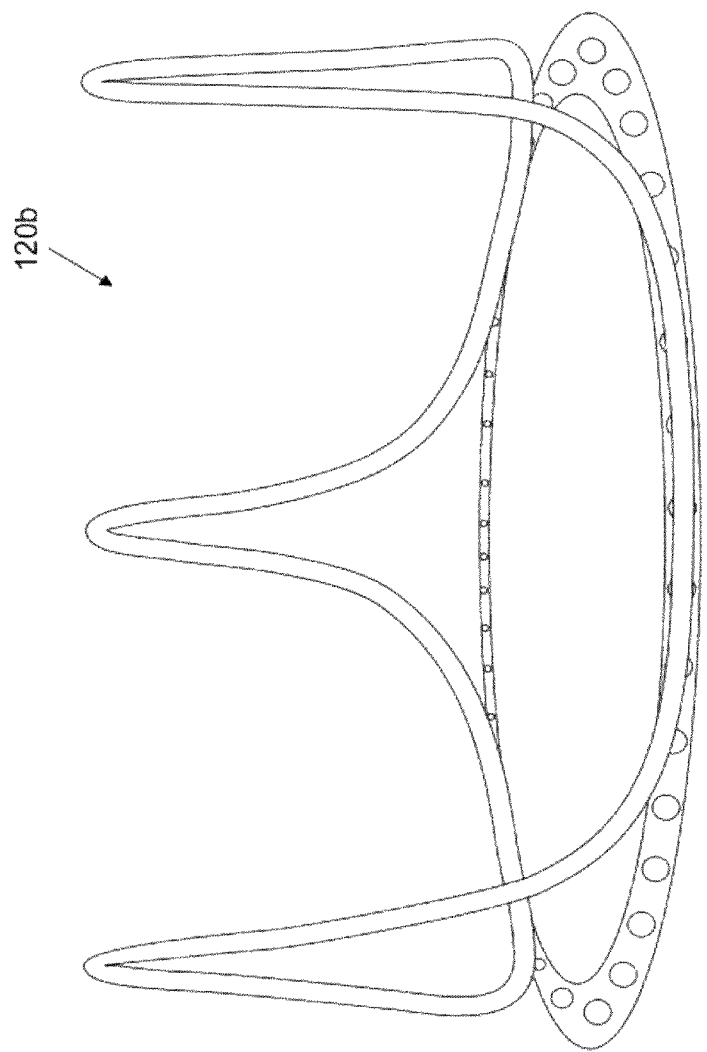
FIG. 10 shows a schematic depiction of a mechanical support structure for the valve cusp with fastening capability on a proximal annular structure.

FIG. 9 shows an alternative implant 12b which can be implanted using an implantation device (not shown), for implantation in an animal body and/or human body, comprising a support frame 46b which has two annular structures 54b, 56b disposed on a distal end 98b and a proximal end 64b of support frame 46b, respectively, and above and below an implantation site 70b or an annulus 76b in axial direction 62b. In this case as well, the two annular structures 54b, 56b are formed of elements 48b which have an expandable region 50b and an expandable cavity 18b that can be expanded by an expansion element 16b which acts as a spring 44b and is composed of a solid body 20b and an elastic wire 42b. A valve 60b, which is designed as aortic valve 74b, is disposed proximally above annular structure 56b in axial direction 62b on proximal end 64b of support structure 46b in the aorta above annulus 76b, and is affixed to annular structure 56b. This arrangement of elements 54b, 56b and 60b one behind the other reduces a diameter of implant 12b during implantation. For upper fixation of cusps 104b of valve 60b, a mechanical support structure 120b in the form of a metal framework composed e.g. of Nitinol (see FIG. 10) is fastened to proximal annular structure 56b or to proximal end 118b of valve 60b. This ensures the relative positioning of annular structure 56b and cusp 104c and ensures that cusp 104b can open and close reliably.

Figure 11:
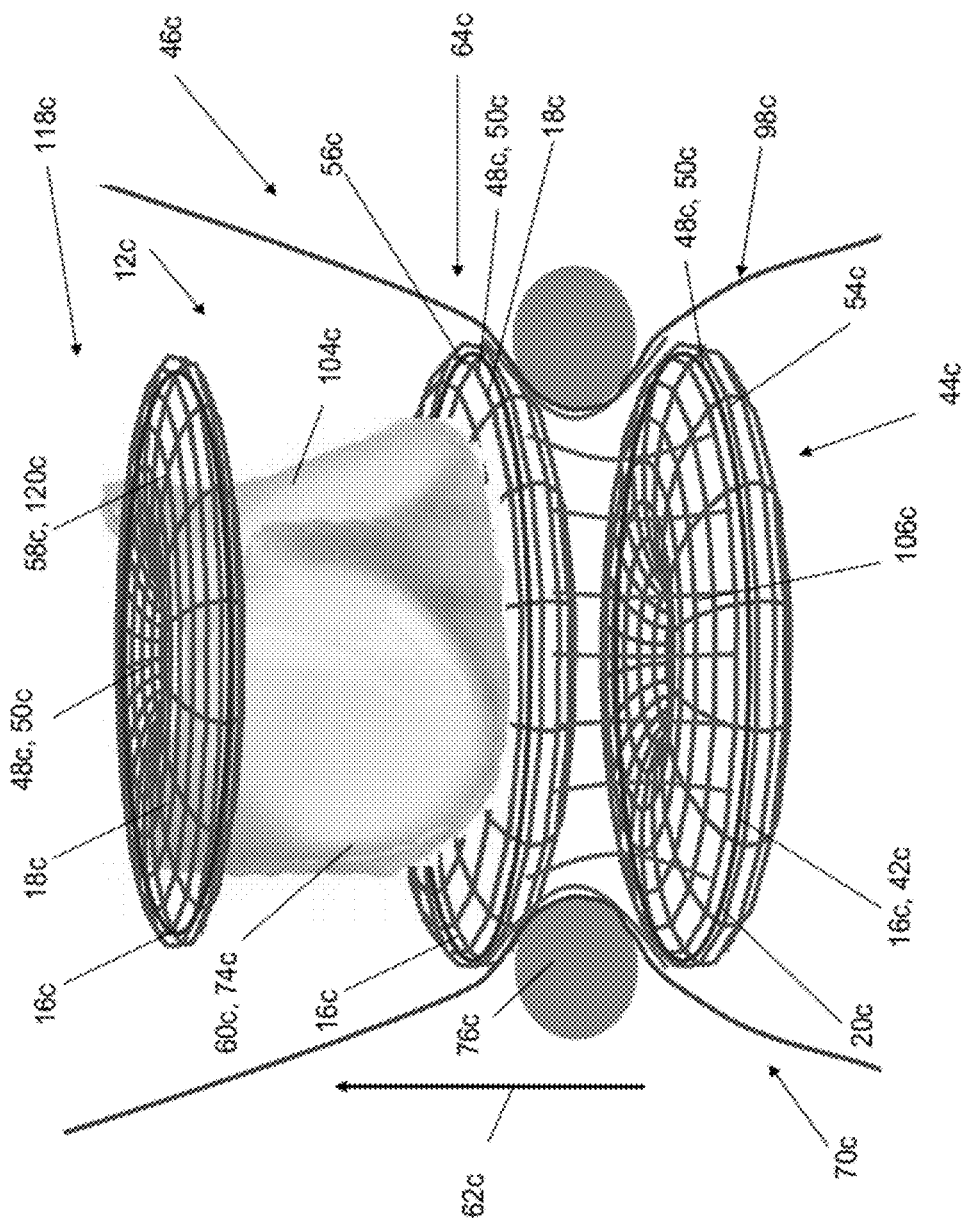
FIG. 11 shows a further alternative implant in the implanted state at an annulus, in a schematic depiction.

FIG. 11 shows a third alternative implant 12c for implantation in an animal and/or human body, comprising an artificial valve 60c or aortic valve 74c and a support frame 46c. Valve 60c is disposed above an annular structure 56c in an axial direction 62c on a proximal end 64c of support frame 46c in the aorta over an implantation site 70c or an annulus 76c. For upper fixation of cusps 104c of valve 60c, a mechanical support structure 120c in the form of a third annular structure 58c is disposed on a proximal end 118c of valve 60c. Annular structure 58c or an element 48c is structurally identical to annular structures 54c, 56c on proximal end 64c and a distal end 98c of support frame 46c. Furthermore, it or a region 50c and cavity 18c thereof can be expanded using the same annular spring mechanism as annular structures 54c, 56c using an expansion element 16c which acts as a spring 44c and is composed of a solid body 20c or an elastic wire 42c. Furthermore, a connecting structure analogous to a connecting structure 106c between annular structures 54c, 56c can be provided between annular structure 58c and one or both of the annular structures Mc, 56c (not shown).

FIG. 12A shows an implantation device 10d designed analogously to implantation device 10a, comprising an implant 12d and an implantation aid 14d disposed in a catheter system 78d which is composed of a delivery element 22d and an expansion element 16d, which are connected by way of a detachable connection 24d designed as a bayonet catch 26d. Implant 12d, which is composed entirely of a support frame 46d designed as annular structure 54d, can be expanded using expansion element 16d which can be inserted into a cavity 18d of support frame 46d of implant 12d, and which is formed by a solid body 20d or an elastic wire 42d, and can be implanted at an implantation site 70d (see FIG. 12B).

Furthermore, implant 12d is designed as a protective structure 72d for temporary implantation as a protection device. For this purpose, it comprises a retaining means 122d formed by a shield composed of a polymeric net on distal end 98d. The protection device can be inserted into the target vessel in the folded state using catheter system 78d. When delivery element 22d is moved forward, annular structure 54d is expanded and the polymeric net, which functions as a protection device, unfolds. When bayonet catch 26d is released, the device remains in the vessel and the catheter can be withdrawn. The protection device can be removed by performing the steps in the reverse order.

It will be apparent to those skilled in the art that numerous modifications and variations of the described examples and embodiments are possible in light of the above teaching. The disclosed examples and embodiments are presented for purposes of illustration only. Other alternate embodiments may include some or all of the features disclosed herein. Therefore, it is the intent to cover all such modifications and alternate embodiments as may come within the true scope of this invention.

LIST OF REFERENCE CHARACTERS

10 Implantation device
12 Implant
14 Implantation aid
16 Expansion element
18 Cavity
20 Solid body
22 Delivery element
24 Connection
26 Bayonet catch
28 Wire
30 End
32 End
34 Body
36 Connecting structure
38 Fastening means
40 Connecting structure
42 Wire
44 Spring
46 Support frame
48 Element
50 Region
52 Guide means
54 Annular structure
56 Annular structure
58 Annular structure
60 Valve
62 Direction
64 End
66 Inner cross-section
68 Cross-sectional area
70 Implantation site
72 Protective structure
74 Aortic valve
76 Annulus
78 Catheter system
80 Valve implant
82 Enclosure
84 Connecting structure
86 End
88 Squared end
90 Wall
92 Circumferential direction
94 Advancing direction
96 Clamping jaw
98 End
100 Flow direction
102 Flow medium
104 Cusp
106 Connecting structure
108 Implantation direction
110 Aortic wall
112 Calcification
114 Funnel
116 Recess
118 End
120 Support structure
122 Retaining means

What is claimed is:
1. An implantation device comprising:
a medical implant in the form of a heart valve;

an expandable annular support connected to the heart valve, the annular support comprising a continuous inner cavity, a recess providing an entrance to the inner cavity and a funnel extending from the recess to access the inner cavity through the recess from outside of the annular support; and at least one implantation aid having at least one expansion element in the form of a wire positioned within the cavity for expanding the annular support, wherein at one end of the wire is a connecting structure configured for detachable connection to a complementary mating structure permitting reconnection after implantation of the medical implant, wherein the connecting structure is positioned within the funnel to close access to the inner cavity by seating at the recess when the at least one implant is in an implanted state.

2. The implantation device according to claim 1, wherein the connecting structure and complementary mating structure comprise a bayonet catch.

3. The implantation device according to claim 1, further comprising a a delivery element formed by an elastic wire.

4. The implantation device according to claim 1, wherein the expansion element further comprises a second connecting structure, for connection to a fastening means of the medical implant, disposed on a distal end of the expansion element.

5. The implantation device according to claim 1, wherein the wire is an elastic wire.

6. The implantation device according to claim 1, wherein the wire functions as a spring having pronounced radial forces.

7. The implantation device according to claim 1, characterized in that the heart valve is disposed proximally above the annular structure in an axial direction on a proximal end of the support.

8. The implantation device according to claim 1, wherein the heart valve is an aortic valve.

9. The implantation device according to claim 1, wherein the annular support is a tubular polymer cylinder.

10. The implantation device according to claim 9, wherein the polymer is polyethylene terephthalate (PET).

11. The implantation device according to claim 1, wherein the expandable annular support is a first annular support, the implantation device further comprising a second expandable annular support, wherein the first and second annular supports are independently expandable.

12. The implantation device according to claim 11, wherein the first and second annular supports are interconnected by a continuous polymer foil.

13. The implantation device according to claim 1, wherein the annular support comprises a curable material inside the inner cavity.

14. The implantation device according to claim 13, wherein the curable material is selected from the group consisting of an acrylate, a methacrylate, a cyanoacrylate, an epoxide, a urethane, an acrylamide, and an acyl acid.

* * * * *